(12) United States Patent
Baroni et al.

(10) Patent No.: US 8,247,404 B2
(45) Date of Patent: Aug. 21, 2012

(54) DERIVATIVES OF 2-OXOALKYL-1-PIPERAZIN-2-ONE, PREPARATION METHOD THEREOF AND THERAPEUTIC USE OF SAME

(75) Inventors: Marco Baroni, Paris (FR); Francoise Bono, Paris (FR); Sandrine Delbary-Gossart, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/966,408

(22) Filed: Dec. 13, 2010

(65) Prior Publication Data

US 2011/0144122 A1    Jun. 16, 2011

Related U.S. Application Data

(63) Continuation of application No. PCT/FR2009/051117, filed on Jun. 12, 2009.

(30) Foreign Application Priority Data

Jun. 13, 2008  (FR) ..................... 08 03298

(51) Int. Cl.
   *A61K 31/497* (2006.01)
   *A61K 31/55*  (2006.01)
   *A01N 43/00*  (2006.01)
   *C07D 401/00* (2006.01)
   *C07D 213/44* (2006.01)
   *C07D 295/00* (2006.01)

(52) U.S. Cl. ............ 514/212.08; 514/253.13; 540/524; 544/364; 546/262; 548/540

(58) Field of Classification Search ............ 514/212.08, 514/253.13; 544/364; 546/262; 548/540; 540/524
See application file for complete search history.

(56) References Cited

U.S. PATENT DOCUMENTS

| | | | |
|---|---|---|---|
| 4,617,309 A * | 10/1986 | Bottcher et al. | 514/339 |
| 6,613,942 B1 * | 9/2003 | Ling et al. | 564/161 |
| 7,423,039 B2 | 9/2008 | Dos Santos et al. | |
| 7,468,368 B2 | 12/2008 | Bono et al. | |
| 7,652,011 B2 | 1/2010 | Bosch et al. | |
| 2007/0021609 A1 * | 1/2007 | Dos Santos et al. | 544/120 |

FOREIGN PATENT DOCUMENTS

| | | |
|---|---|---|
| WO | WO 97/28140 | 8/1997 |
| WO | WO/97/28140 * | 8/1997 |
| WO | WO 99/01423 | 1/1999 |
| WO | WO 00/59893 | 10/2000 |
| WO | WO 03/104225 | 12/2003 |
| WO | WO 2005/054227 | 6/2005 |
| WO | WO 2005/054229 | 6/2005 |
| WO | WO 2009/150387 A1 | 12/2009 |

OTHER PUBLICATIONS

Weskamp, G., et al., Evidence That Biological Activity of NGF is Mediated Through a Novel Subclass of High Affinity Receptors, Neuron, vol. 6, pp. 649-663, (1991).

Della-Bianca, V., et al., Neurotrophin P75 Receptor is Involved in Neuronal Damage by Prion Peptide-(106-126). The Journal of Biological Chemistry, vol. 276, No. 42, (2001), pp. 38929-38933.

Friedman, W. J., et al., Neurotrophin Signaling Via Trks and P75, Experimental Cell Research, vol. 253, pp. 131-142, (1999).

Longo, F. M., et al., Small Molecule Neurotrophin Receptor Ligands: Novel Strategies for Targeting Alzheimer's Disease Mechanisms, Current Alzheimer Research, (2007), vol. 4, pp. 503-506.

Lowry, K., et al., A Potential Role for the P75 Low-Affinity Neurotrophin Receptor in Spinal Motor Neuron Degeneration in Murine and Human Amyotrophic Lateral Sclerosis, Amyotroph. Lateral. Scler. (2001), vol. 2, pp. 127-134.

Perlman, H., et al., Evidence for the Rapid Onset of Apoptosis in Medial Smooth Muscle Cells After Balloon Injury, Circulation, (1997), vol. 95, pp. 981-987.

Rabizadeh, S., et al., Expression of the Low-Affinity Nerve Growth Factor Receptor Ennances B-Amyloid Peptide Toxicity, Proc. Natl. Acad. Sci. USA, vol. 91, pp. 10703-10706, (1994).

Raychaudhuri, S. P., et al., Role of NGF and Neurogenic Inflammation in the Pathogenesis of Psoriasis, Progress in Brain Research, vol. 146, pp. 433-437, (2004).

Rihl, M., et al, Involvement of Neurotrophins and Their Receptors in Spondyloarthritis Synovitis: Relation to Inflammation and Response to Treatment, Ann Rheum Dis, (2005), vol. 64, pp. 1542-1549.

Roux, P. P., et al, P75 Neurotrohpin Receptor Expression is Induced in Apoptotic Neurons After Seizure, The Journal of Neuroscience, (1999), vol. 19, No. 16, pp. 6887-6896.

Sanguinetti, M. C., et al., HERG Potassium Channels and Cardiac Arrhythmia, Nature, vol. 440, pp. 463-469, (2006).

Tokuoka, S., et al., Disruption of Antigen-Induced Airway Inflammation and Airway Hyper-Responsiveness in Low Affinity Neurotrophin Receptor P75 Gene Deficient Mice, British Journal of Pharmacology, (2001), vol. 134, pp. 1580-1586.

Chaldakov, G. N., et al., Neurotrophin Presence in Human Coronary Atherosclerosis and Metabolic Syndrome: a Role for NGF and BDNF in Cardiovascular Disease, Progress in Brain Research, vol. 146, pp. 279-289, (2004).

* cited by examiner

*Primary Examiner* — Andrew D Kosar
*Assistant Examiner* — Erich A Leeser
(74) *Attorney, Agent, or Firm* — Ronald G. Ort; Kelly L. Bender

(57) ABSTRACT

The present invention relates to derivatives of 4-{2-[phenyl-3,6-dihydropyridin-1-yl]-2-oxoalkyl}-1-piperazin-2-one and 4-{2-[phenyl-2,5-dihydropyrrol-1-yl]-2-oxoalkyl}-1-piperazin-2-one having general formula (I):

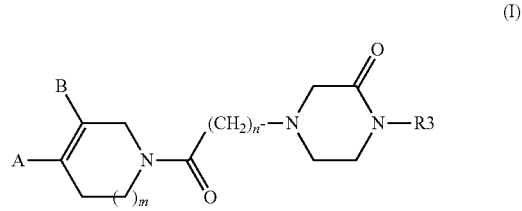

(I)

in which A, B, m, R3 and n are as defined herein. The invention also relates to the preparation thereof and to the therapeutic use thereof.

11 Claims, No Drawings

DERIVATIVES OF 2-OXOALKYL-1-PIPERAZIN-2-ONE, PREPARATION METHOD THEREOF AND THERAPEUTIC USE OF SAME

The present invention relates to 4-{2-[phenyl-3,6-dihydropyridin-1-yl]-2-oxoalkyl}-1-piperazin-2-one and 4-{2-[phenyl-2,5-dihydropyrrol-1-yl]-2-oxoalkyl}-1-piperazin-2-one derivatives, to the preparation thereof and to the therapeutic use thereof.

The compounds according to the present invention have an affinity for the p75$^{NTR}$ neurotrophin receptor.

Neurotrophins belong to a family of proteins of which the biological effect is in particular cell survival and differentiation.

The p75$^{NTR}$ receptor, the receptor for all neurotrophins, is a transmembrane glycoprotein of the tumour necrosis factor (TNF) receptor family (W. J. Friedman and L. A. Greene, Exp. Cell. Res., 1999, 253, 131-142). The p75$^{NTR}$ receptor is expressed in several cell types, and several biological functions have been attributed to said receptor: on the one hand, modulation of the affinity of neurotrophins for tyrosine kinase (trk) receptors; on the other hand, in the absence of trk, induction of a signal for cell death by apoptosis. Moreover, the neurotrophin precursors, proneurotrophins, are capable of binding to p75$^{NTR}$ with a high affinity, and are considered to be powerful p75$^{NTR}$-dependent inducers of apoptosis in neurons and certain cell lines.

At the level of the central nervous system, many studies show that apoptosis occurs in several pathological conditions, such as amyotrophic lateral sclerosis, multiple sclerosis, Alzheimer's disease, Parkinson's disease and Huntington's disease and prion diseases. P75$^{NTR}$ is also known to be overexpressed in various types of neurodegenerative diseases, such as Alzheimer's disease and amyotrophic lateral sclerosis (ALS) (Longo F. M. et al., Curr. Alzheimer Res. 2007; 4: 503-506; Lowry K. S. et al., Amyotroph. Lateral. Scler. Other. Motor. Neuron. Disord. 2001; 2:127-34).

Results suggest that p75$^{NTR}$ may play a predominant role in the mechanisms resulting in post-ischaemic apoptotic neuron death (P. P. Roux et al., J. Neurosci., 1999, 19, 6887-6896).

Results (V. Della-Bianca et al., J. Biol. Chem., 2001, 276: 38929-33), (S. Rabizadeh et al., Proc. Natl. Acad. Sci. USA, 1994, 91, 10703-10706) support the hypothesis that p75$^{NTR}$ plays an important role in neuron death induced by prion protein infections (transmissible spongiform encephalopathy) or by beta-amyloid protein (Alzheimer's disease).

The p75$^{NTR}$ receptor is also associated with the Nogo receptor and involved in the signalling of the inhibitory effects of these myelin proteins on axon growth. As a result the p75$^{NTR}$ receptor plays a major role in the regulation of the neuronal plasticity and in neuron-glia interactions, and thus represents a therapeutic target of choice for promoting nerve regeneration.

Beyond the nervous system and neurodegenerative diseases, it has been suggested that p75$^{NTR}$ could play a role in cardiovascular diseases, such as atherosclerosis and myocardial ischaemia (M. L. Bochaton-Pialat et al., Am. J. Pathol., 1995, 146, 1-6; H. Perlman, Circulation, 1997, 95, 981-987). Recent studies show an increase in the expression of p75$^{NTR}$ and of neurotrophins, and a massive apoptosis in atherosclerosis lesions.

Several studies also suggest that p75$^{NTR}$ is an inflammation mediator (Rihl M. et al., Ann. Rheum. Dis. 2005; 64(11): 1542-9; Raychaudhuri S. P. et al., Prog. Brain. Res. 2004; 146: 433-7, Tokuoka S. et al., Br. J. Pharmacol. 2001, 134: 1580-1586).

P75$^{NTR}$ also plays an essential role in tumour biology.

Many compounds are known to interact with the trkA/NGF/p75$^{NTR}$ system or to have an NGF-type (nerve grown factor) activity. Thus patent application WO 00/59893 describes substituted pyrimidine derivatives which have an NGF-type activity and/or which increase the activity of NGF on PC12 cells.

Patent application WO 03/104225 describes compounds which exhibit affinity for P75$^{NTR}$ receptors. These compounds are highly metabolized and exhibit high percentages of inhibition of the hERG gene (the human Ether-a-go-go Related Gene).

The hERG gene encodes the $K_v11.1$. protein of a potassium ion channel. This protein is known for its contribution to the electrical activity of the heart. When the ability of the channel to conduct the electric current through the cell membrane is inhibited by the action of medicaments, it may result in a potentially fatal disorder called QT syndrome. A certain number of medicaments have inhibited this protein, creating a concomitant risk of sudden death as an adverse side effect. This has made hERG inhibition a central question both in the regulation of medicaments and in the development thereof (Sanguinetti MC, Tristani-Firouzi M (March 2006). "hERG potassium channels and cardiac arrhythmia". Nature 440 (7083): 463-9).

A subject of the present invention is novel compounds which exhibit affinity for P75$^{NTR}$ receptors and which do not have the drawbacks of high metabolization and of strong hERG inhibition that the prior art compounds have. It therefore provides an advantage for the development of new medicaments.

A subject of the present invention is the compounds corresponding to the formula (I):

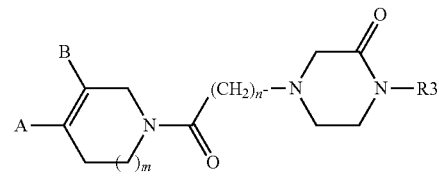

in which:
m is 0 or 1;
A is:

R2—⟨ring with R1⟩ and B is a hydrogen atom or
A is a hydrogen atom and B is:

R2—⟨ring with R1⟩;

R1 and R2, which may be identical or different, are independently a hydrogen or halogen atom, a $C_1$-$C_4$alkyl, $C_1$-$C_4$fluoroalkyl, $C_1$-$C_2$perfluoroalkyl or $C_1$-$C_4$alkoxy group or a trifluoromethoxy group;

n is 1 or 2;

R3 is a group of formula:

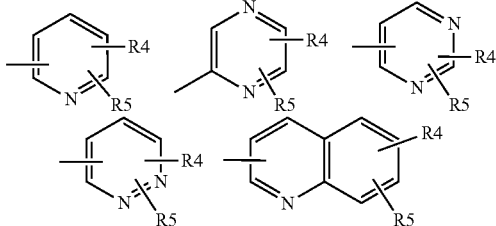

where R4 and R5, which may be identical or different, are located on any available positions and are independently a hydrogen or halogen atom, a hydroxyl, a $C_1$-$C_4$alkyl, $C_1$-$C_4$fluoroalkyl, $C_1$-$C_2$perfluoroalkyl or $C_1$-$C_4$alkoxy group, a trifluoromethoxy group, a cyano group, or a COOH, COOalkyl, $CONH_2$, CONR6R7 or NHCOR group;

R, R6 and R7 are a $C_1$-$C_6$alkyl.

The compounds of formula (I) may comprise one or more asymmetrical carbon atoms. They may therefore exist in the form of enantiomers or diastereoisomers. These enantiomers and diastereoisomers and also mixtures thereof, including racemic mixtures, form part of the invention.

The compounds of formula (I) may exist in the form of bases or of addition salts with acids. Such addition salts form part of the invention.

These salts may be prepared with pharmaceutically acceptable acids, but the salts of other acids that are useful, for example, for purifying or isolating the compounds of formula (I) also form part of the invention.

In the context of the present invention:

the term "a halogen atom" is intended to mean: a fluorine, a chlorine, a bromine or an iodine;

the term "an alkyl group" is intended to mean: a linear or branched, saturated aliphatic group. By way of examples, mention may be made of a $C_1$-$C_4$alkyl group which may represent a methyl, ethyl, propyl, isopropyl, butyl, isobutyl or tert-butyl;

the term "a fluoroalkyl group" is intended to mean: an alkyl group of which one or more hydrogen atoms have been substituted with a fluorine atom;

the term "a perfluoroalkyl group" is intended to mean: an alkyl group of which all the hydrogen atoms have been substituted with a fluorine atom;

the term "an alkoxy group" is intended to mean: an —O— alkyl group where the alkyl group is as defined above.

Among the compounds of formula (I) which are subjects of the invention, another group of compounds is constituted of those for which R4 and R5, which may be identical or different, are located on any available positions, and are independently $CONH_2$, CONR6R7 or NHCOR, R, R6 and R7 being defined as above;

in the form of bases or of addition salts with acids.

Among the compounds of formula (I) which are subjects of the invention, another group of compounds is constituted of the compounds of formula (I) in which:

m is 1;

A is:

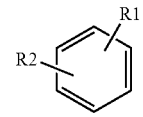

and B is a hydrogen atom;

R1 and R2, which may be identical or different, are independently a hydrogen or halogen atom, a $C_1$-$C_4$alkyl, $C_1$-$C_4$fluoroalkyl, $C_1$-$C_2$perfluoroalkyl or $C_1$-$C_4$alkoxy group or a trifluoromethoxy group;

n is 1 or 2;

R3 is a group of formula:

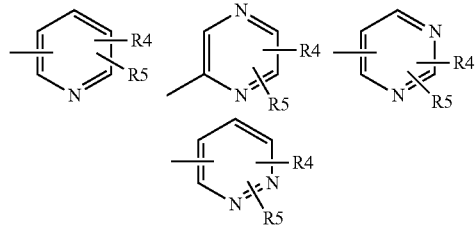

where R4 and R5, which may be identical or different, are located on any available positions and are independently a hydrogen or halogen atom, a hydroxyl, a $C_1$-$C_4$alkyl, $C_1$-$C_4$fluoroalkyl, $C_1$-$C_2$perfluoroalkyl or $C_1$-$C_4$alkoxy group, a trifluoromethoxy group, a cyano group, or a COOH or COOalkyl group; in the form of bases or of addition salts with acids.

Among the compounds of formula (I) which are subjects of the invention, another group of compounds is constituted of those for which R1 is other than H, R2 being as defined above; in the form of bases or of addition salts with acids.

Among the compounds of formula (I) which are subjects of the invention, another group of compounds is constituted of the compounds for which:

R1 is in position-2-, -3- or -4- of the phenyl and is a halogen atom or more particularly a chlorine atom, or a $CF_3$ radical, and R2 is a hydrogen or a 3- or 4-halogen, more particularly a 3- or 4-Cl; or else R1 is in position 2-, 3- or 4- and is a chlorine atom or a $CF_3$ radical and R2 is a hydrogen atom; or else R1 is in position 3- of the phenyl and is a $CF_3$ radical, and R2 is in position 4- of the phenyl and is a chlorine atom; or else R1 is in position 2- of the phenyl atom and is a chlorine atom, and R2 is in position 3- of the phenyl and is a chlorine atom; and/or R3 is a 2-pyridynyl or a 2-pyrimidinyl, each substituted with R4 and R5 as defined above; and/or n=1;

in the form of bases or of addition salts with acids.

Among the compounds of this latter group, mention may be made of the compounds of formula (I) for which:

R1 is 3-$CF_3$;

R2 is 4-chloro;

R3 is a 2-pyridyl residue 5-substituted with a $CF_3$; and n=1;

in the form of bases or of addition salts with acids.

Among the compounds of formula (I) which are subjects of the invention, mention may in particular be made of the following compounds:

Compound No. 1: 4-{2-[4-(4-chloro-3-trifluoromethylphenyl)-3,6-dihydro-2H-pyridin-1-yl]-2-oxoethyl}-1-(5-trifluoromethylpyridin-2-yl)piperazin-2-one;
Compound No. 2: 4-{2-[4-(4-chloro-3-trifluoromethylphenyl)-3,6-dihydro-2H-pyridin-1-yl]-2-oxoethyl}-1-(5-methylpyridin-2-yl)piperazin-2-one;
Compound No. 3: 4-{2-[4-(4-chlorophenyl)-3,6-dihydro-2H-pyridin-1-yl]-2-oxoethyl}-1-(5-trifluoromethylpyridin-2-yl)piperazin-2-one;
Compound No. 4: 4-{2-oxo-2-[4-(3-trifluoromethylphenyl)-3,6-dihydro-2H-pyridin-1-yl]ethyl}-1-pyridin-2-ylpiperazin-2-one;
Compound No. 5: 4-{2-[4-(4-chloro-3-trifluoromethylphenyl)-3,6-dihydro-2H-pyridin-1-yl]-2-oxoethyl}-1-pyridin-2-ylpiperazin-2-one;
Compound No. 6: 4-{2-[4-(4-chlorophenyl)-3,6-dihydro-2H-pyridin-1-yl]-2-oxoethyl}-1-pyridin-2-yl-piperazin-2-one;
Compound No. 7: 4-{2-[4-(2,3-dichlorophenyl)-3,6-dihydro-2H-pyridin-1-yl]-2-oxoethyl}-1-(5-trifluoromethylpyridin-2-yl)piperazin-2-one;
Compound No. 8: 4-{2-[4-(4-chlorophenyl)-3,6-dihydro-2H-pyridin-1-yl]-2-oxoethyl}-1-(6-chloropyridin-2-yl)piperazin-2-one;
Compound No. 9: 4-{2-[4-(3-chlorophenyl)-3,6-dihydro-2H-pyridin-1-yl]-2-oxoethyl}-1-(5-trifluoromethylpyridin-2-yl)piperazin-2-one;
Compound No. 10: 4-{2-[4-(4-trifluoromethylphenyl)-3,6-dihydro-2H-pyridin-1-yl]-2-oxoethyl}-1-(5-trifluoromethylpyridin-2-yl)piperazin-2-one;
Compound No. 11: 4-{2-[4-(3-trifluoromethylphenyl)-3,6-dihydro-2H-pyridin-1-yl]-2-oxoethyl}-1-(5-trifluoromethylpyridin-2-yl)piperazin-2-one;
Compound No. 12: 4-{2-[4-(4-chloro-3-trifluoromethylphenyl)-3,6-dihydro-2H-pyridin-1-yl]-2-oxoethyl}-1-pyridin-3-ylpiperazin-2-one;
Compound No. 13: 1-(6-chloropyridin-3-yl)-4-{2-[4-(4-chloro-3-trifluoromethylphenyl)-3,6-dihydro-2H-pyridin-1-yl]-2-oxoethyl}piperazin-2-one;
Compound No. 14: 4-{2-oxo-2-[5-(3-trifluoromethylphenyl)-3,6-dihydro-2H-pyridin-1-yl]ethyl}-1-(5-trifluoromethylpyridin-2-yl)piperazin-2-one;
Compound No. 15: 4-{2-oxo-2-[4-(3-trifluoromethoxylphenyl)-3,6-dihydro-2H-pyridin-1-yl]ethyl}-1-pyridin-2-ylpiperazin-2-one;
Compound No. 16: 4-{2-[4-(4-chloro-3-trifluoromethylphenyl)-2,5-dihydro-pyrrol-1-yl]-2-oxoethyl}-1-(5-trifluoromethylpyridin-2-yl)piperazin-2-one;
Compound No. 17: 4-{2-[4-(3,5-bistrifluoromethylphenyl)-3,6-dihydro-2H-pyridin-1-yl]-2-oxoethyl}-1-(5-trifluoromethylpyridin-2-yl)piperazin-2-one;
Compound No. 18: 4-{2-[4-(3-methylphenyl)-3,6-dihydro-2H-pyridin-1-yl]-2-oxoethyl}-1-(5-trifluoromethylpyridin-2-yl)piperazin-2-one;
Compound No. 19: 4-{2-[4-phenyl-3,6-dihydro-2H-pyridin-1-yl]-2-oxoethyl}-1-(5-trifluoromethylpyridin-2-yl)piperazin-2-one;
Compound No. 20: 4-{2-oxo-2-[5-(2,3-dichlorophenyl)-3,6-dihydro-2H-pyridin-1-yl]ethyl}-1-(5-trifluoromethylpyridin-2-yl)piperazin-2-one;
Compound No. 21: 4-{2-oxo-2-[5-(3-methoxyphenyl)-3,6-dihydro-2H-pyridin-1-yl]ethyl}-1-(5-trifluoromethylpyridin-2-yl)piperazin-2-one;
in the form of bases or of addition salts with acids.

In the subsequent text, the term "protective group Pg" is intended to mean a group makes it possible, on the one hand, to protect a reactive function such as a hydroxyl or an amine during a synthesis and, on the other hand, to regenerate the intact reactive function at the end of synthesis. Examples of protective groups and also of the methods of protection and of deprotection are given in "Protective Groups in Organic Synthesis", Green et al., 2nd Edition (John Wiley & Sons, Inc., New York).

In accordance with the invention, the compounds of general formula (I) are prepared according to the process which follows.

Scheme 1:

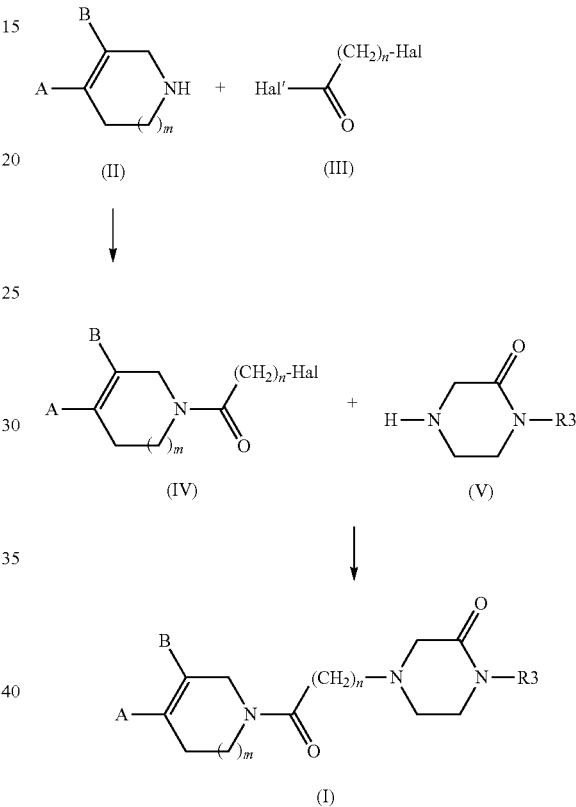

The compounds of formula (I) in which A, B, m, n and R3 are as defined above, can be prepared by reaction of a compound of formula (IV) as defined above, with a compound of formula (V) as defined above according to methods known to those skilled in the art as described in WO03/104225. More particularly, the process for preparing the compounds of general formula (I) comprises the reaction of a compound of formula (IV):

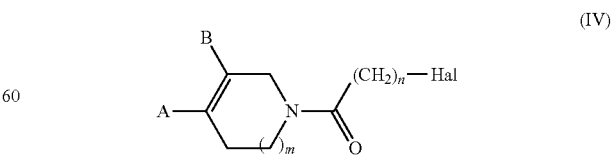

(IV)

in which A, B, m and n are as defined in general formula (I) and Hal represents a halogen atom, for example chlorine, and of a compound of general formula (V):

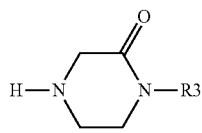

in which R3 is as defined in general formula (I) in the presence of a base, in a solvent as described in WO 03/104225. Thus, by way of base, mention may be made of organic bases such as triethylamine, N,N-diisopropylamine, diisopropylethylamine (DPEA), or N-methylmorpholine or alkali metal carbonates or bicarbonates such as potassium carbonate, sodium carbonate or sodium bicarbonate and in the absence or in presence of an alkali metal iodide such as potassium iodide or sodium iodide. The reaction is carried out favourably in a solvent such as acetonitrile, N,N-dimethylformamide (DMF), N-methylpyrrolidone (NMP), toluene or propan-2-ol, at a temperature between ambient temperature and the reflux temperature of the solvent. The term "ambient temperature" is intended to mean a temperature between 5 and 25° C. By way of example, the reaction may be carried out in the presence of sodium bicarbonate, and sodium iodide in a solvent such as DMF. The reaction is preferably carried out in a microwave reactor.

In the products of general formula (I) thus obtained, R, R1, R2, R4, R5, R6, and R7 can be modified by treatments commonly used by those skilled in the art, such as, for example, by hydrolysis of an ester group to give a carboxylic group.

The addition salts with an acid of the compounds of general formula (I) may be obtained by addition of the appropriate acid to the compound of formula (I) in the free base form.

The compounds of formula (IV), in which R1 and R2 are as defined for the compounds of formula (I), can be prepared by reaction of a compound of formula (II) with a compound of formula (III) according to methods known to those skilled in the art for example in presence of a base in a solvent as described in WO03/104225.

More particularly, the compounds of formula (IV) can be obtained by reaction of a corresponding compound of formula (II):

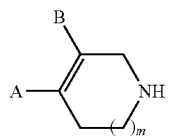

in which A, B and m are defined as in general formula (I); optionally in the form of an addition salt with an acid, and of a compound of formula (III):

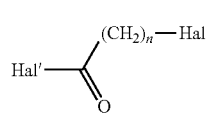

in which n and Hal are as defined in formula (IV) and Hal' is a halogen atom, which may be identical or different. Preferably, Hal' is a chlorine atom.

This reaction is generally carried out in the presence of a base, such as triethylamine, N,N-diisopropylethylamine or N-methylmorpholine, in a solvent such as dichloromethane, chloroform, tetrahydrofuran or dioxane or a mixture of these solvents and at a temperature of between 0° C. and ambient temperature. The compounds of formulae (II) and (III) are generally commercially available or can be prepared according to methods known to those skilled in the art.

The compounds of the formula (V), in which R3 is as defined in formula (I), are prepared according to methods known to those skilled in the art. They can be prepared, for example, according to the process which follows:

Scheme 2:

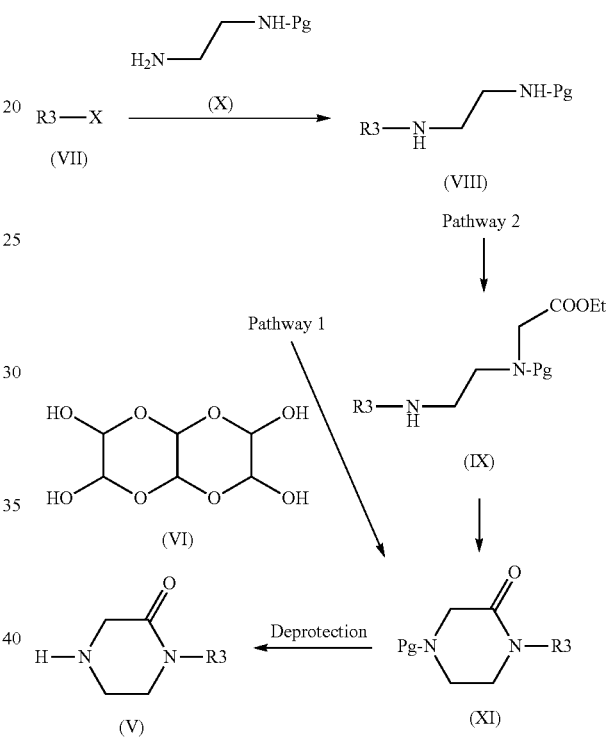

More particularly, the compound of formula (V) can be prepared from a corresponding compound of formula (XI), in which R3 is as defined in formula (I) and Pg is a protective group for the nitrogen atom, such as benzyl. This reaction can be carried out by application or adaptation of any method known to those skilled in the art; generally, this reaction is carried out in an acidic medium, in the presence of a catalyst, such as Pd/C.

The compound of formula (XI) can be obtained from a compound of formula (VIII) in which R3 is as defined in formula (I) and Pg is a protective group, in the presence of a compound of formula (VI). Generally, this reaction is carried out at a temperature between ambient temperature and the boiling point of the reaction mixture that may comprise water.

Alternatively, the compound of formula (XI) can be obtained from a compound of formula (IX) by reaction with alkaline hydrides in inert solvents such as toluene, dimethylformamide or dimethyl sulphoxide, at a temperature of between ambient temperature and the boiling point of the reaction mixture.

The compound of formula (IX) can be obtained from a compound of formula (VIII) by reaction with ethyl bromoacetate or ethyl chloroacetate in solvents such as butanol or acetone, in the presence of a base such as potassium carbonate, at a temperature of between ambient temperature and the boiling point of the reaction mixture.

The compound of formula (VIII) can be obtained from a compound of formula (VII) in which R3 is as defined in formula (I) and X is a halogen atom, such as chlorine, in the presence of a compound of formula (X) in which Pg is a protective group as defined in formula (VIII). Generally, this reaction is carried out at a temperature between ambient temperature and the boiling point of the reaction mixture.

Optionally, the process according to the invention comprises the subsequent step consisting in isolating the desired product obtained.

According to another of its aspects, a subject of the invention is also compounds of formula (IV)

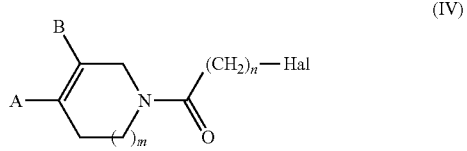

in which A, B, m and n are defined as in general formula (I) and Hal is a halogen atom, for example chlorine; in the form of bases or of addition salts with acids.

These compounds are of use as intermediates for synthesizing the compounds of formula (I).

The starting compounds and the reactants, in Schemes 1 and 2, when the method for the preparation thereof is not described, are commercially available or described in the literature, or else can be prepared according to methods which are described therein or which are known to those skilled in the art.

The following examples describe the preparation of certain compounds in accordance with the invention. These compounds are not limiting and merely illustrate the present invention. The numbers of the compounds exemplified refer back to those given in the table hereinafter, which illustrates the chemical structures and the physical properties of some compounds according to the invention.

The HPLC has been carried out using a ThermoElectron LCQ Deca XP Max system equipped with a mass spectrometry ion trap detector and a diode array detector.

The conditions for analysis by liquid chromatography coupled to mass spectrometry (LC/UV/MS) are the following:
chromatographic system A
Eluent A=$H_2O$+0.01% TFA
Eluent B=$CH_3CN$
Gradient of 98% of A to 95% of B in 10 minutes, then elution with 95% of B for 5 minutes.
Flow rate 0.5 ml/minute; temperature 40° C.
Injection of 2 µL of solution at 0.1 mg/ml in a mixture of $CH_3CN:H_2O$=9:1
chromatographic system B
Eluent A=$H_2O$+0.05% TFA
Eluent B=$CH_3CN$+0.035% TFA
Gradient of 98% of A to 95% of B in 12 minutes, then elution with 95% of B for 3 minutes.
Flow rate 0.7 ml/minute; temperature 40° C.
Injection of 2 µL of solution at 0.1 mg/ml in a mixture of $CH_3CN:H_2O$=9:1-chromatographic system C
Eluent A=ammonium acetate buffer 5 mM pH 6.5
Eluent B=$CH_3CN$
Gradient of 98% of A to 95% of B in 10 minutes, then elution with 95% of B for 5 minutes.
Flow rate 0.5 ml/minute; temperature 40° C.
Injection of 2 µL of solution at 0.1 mg/ml in a mixture of $CH_3CN:H_2O$=9:1
The products are detected by UV at 220 nm.
The columns used are C18 columns with a particle size between 2 and 4 µm, preferably 3.5 µm.
For the mass spectrometry part:
Ionization mode: positive electrospray (API-ES polarity+)
Scanning from 120 to 1500 uma
The proton nuclear magnetic resonance ($^1H$ NMR) spectra were recorded under the following conditions:
a) at 500 MHz on a Bruker machine equipped with an Avance III console;
b) at 400 MHz on a Bruker machine equipped with an Avance I console.

The chemical shifts are recorded in ppm with respect to the TMS frequency.

The abbreviations used to characterize the signals are the following: s=singlet, bs=broad singlet, m=multiplet, bm=broad multiplet, d=doublet, bd=broad doublet, t=triplet, q=quadruplet.

*=not integratable because of interference with a broad peak due to water.

**=not integratable because of interference with a peak due to the NMR solvent.

2×m=two partially superimposed multiplets.

Preparation 1

1-(5-Trifluoromethylpyridin-2-yl)piperazin-2-one hydrochloride 10 g of 2-chloro-5-(trifluoromethyl)pyridine (compound of formula (VII)) and 40.5 ml of N-benzylethylenediamine (compound of formula (X)) are heated at 135° C. for 6 hours in a round-bottomed flask. The mixture is poured into water and the resulting mixture is extracted with ethyl acetate. The resulting product is dried and evaporated to dryness; the crude product thus obtained is purified by flash chromatography. The isolated product (compound of formula (VIII)), 14 g, is solubilized in 200 ml of a 2N solution of HCl. 30 g of trimeric glyoxal dihydrate (compound VI), are added and the mixture is left stirring at ambient temperature for 72 hours. It is extracted with ethyl acetate. The resulting product is dried and evaporated to dryness; the crude product thus obtained is purified by flash chromatography. The isolated product (compound of formula (IX)), 10 g, is solubilized in 450 ml of ethanol, and then 15 ml of a solution of isopropanol saturated with HCl and 3 g of Pd/C at 10% are added. The mixture is left to react under a hydrogen stream for 4 hours at a temperature of 40° C. The resulting product is filtered and evaporated to dryness and 3 g of the title compound are obtained (compound of formula (V)) Melting point 205-207° C.

Preparation 2

1-(5-Methylpyridin-2-yl)piperazin-2-one hydrochloride 4.7 g of 2-chloro-5-methylpyridine (compound of formula (VII)) and 27.5 ml of N-benzylethylenediamine (compound of formula (X)) are heated at 135° C. for 5 hours in a round-bottomed flask. The mixture is poured into water and the resulting mixture is extracted with ethyl acetate. The resulting product is dried and evaporated to dryness; the crude product thus obtained is purified by flash chromatography. A product of 3.6 g is isolated (compound of formula (VIII)).

1.5 g of this product are solubilized in 3 ml of butanol. 0.85 g of potassium carbonate and 1.05 g of ethyl bromoacetate are added and the mixture is heated at reflux temperature for 3 hours. It is poured into water and extracted with ethyl acetate. The resulting product is dried and evaporated to dryness; the crude product thus obtained (2 g) is purified by flash chromatography. The isolated product (compound of formula (IX)), 1 g, is then solubilized in toluene and then this solution is slowly added, under a stream of nitrogen, to a suspension of 0.25 g of sodium hydride at 60% (NaH) in 25 ml of toluene. The mixture is heated at the reflux temperature for 2 hours. It is poured into water and the resulting mixture is extracted with ethyl acetate. The resulting product is dried and evaporated under vacuum.

0.6 g of crude product is obtained in the form of an oil (compound of formula (IX)) which is solubilized in 25 ml of ethanol, and then 1.5 ml of a solution of isopropanol saturated with HCl and 0.3 g of 10% Pd/C are added. The mixture is left to react under a hydrogen stream for 4 hours at a temperature of 40° C. The resulting product is filtered and evaporated under vacuum, and 0.3 g of the compound of the title (compound of formula (V)) is obtained.

Preparation 3

2-Chloro-1-[4-[3-trifluoromethyl-4-chlorophenyl]-1-[3,6-dihydro-1(2H)pyridinyl]]-1-ethanone 4-[3-(Trifluoromethyl)-4-chlorophenyl]-3,6-dihydro-1(2H)-pyridine hydrochloride (compound of formula (II)) (3.94 g) and 3.8 ml of triethylamine in 33.5 ml of dichloromethane are cooled to 0° C. 2-Chloroacetyl chloride (compound of formula (III)) is added dropwise and the mixture is left stirring for 1 h 30. Water is added and the resulting mixture is extracted with dichloromethane. The organic phase is dried over $Na_2SO_4$, filtered and evaporated under vacuum.

4.2 g of the compound are obtained in the form of an amorphous solid (compound of formula (IV)).

EXAMPLE 1

Compound No. 1: 4-{2-[4-(4-chloro-3-trifluoromethylphenyl)-3,6-dihydro-2H-pyridin-1-yl]-2-oxoethyl}-1-(5-trifluoromethylpyridin-2-yl)piperazin-2-one and the hydrochloride thereof A mixture of compound of preparation 3 (0.49 mg), compound of preparation 1 (0.4 mg), potassium carbonate (0.41 g), and sodium iodide (0.45 g) in 7 ml of dimethylformamide is heated in a microwave reactor at 180° C. for 30 minutes. The reaction mixture is poured into water and the resulting mixture is extracted with ethyl acetate. The organic phase is dried over $Na_2SO_4$, filtered and evaporated, to give 700 mg of crude product in the form of an oil. The product is purified by silica gel column chromatography, elution being carried out with a mixture of cyclohexane/ethyl acetate=1/1. The hydrochloride is prepared by adding a solution of hydrochloric acid in isopropanol. 200 g of the title compound are obtained.

$M+H^+=m/z$ 547

δ (ppm, dmso-d6): 2.55 (bs, \*\*); 2.63 (m, \*\*); 3.43-3-54 (m, 2H); 3.65 (m, \*); 3.75 (m, 1H); 3.96 (bs, 2H); 4.18 (m, 6H); 6.40 (bs, 1H); 7.72 (d, J=8.4 Hz, 1H), 7.74-7.80 (m, 1H), 7.80-7.85 (m, 1H), 8.21 (d, J=9 Hz, 1H); 8.26 (dd, $J_1$=9 Hz, $J_2$=2 Hz, 1H); 8.88 (s, 1H).

EXAMPLE 2

Compound No. 2: 4-{2-[4-(4-chloro-3-trifluoromethylphenyl)-3,6-dihydro-2H-pyridin-1-yl]-2-oxoethyl}-1-(5-methylpyridin-2-yl)piperazin-2-one and the hydrochloride thereof The compound of the title is obtained by carrying out the procedure as described in Example 1, but using the compound of preparation 2 in place of the compound of preparation 1.

$M+H^+=m/z$ 493

(Machine a). δ (ppm, dmso-d6): 2.32 (s, 3H), 2.56 (m, 1H), 2.65 (m, 1H), 3.10-3.60 (m, \*), 3.64 (m, 1H), 3.77 (m, 1H), 3.98 (m, 2H), 4.05-4.51 (m, 6H), 6.41 (m, 1H), 7.69 (dd, J=8.4 and 2.0 Hz, 1H), 7.73 (d, 8.5 Hz, 1H), 7.75-7.81 (m, 2H), 7.83 (bd, J=9.3 Hz, 1H), 8.31 (bd, J=2 Hz, 1H).

The table which follows illustrates the chemical structures and the physical properties of some examples of compounds according to the invention. In this table:

in the "salt" column, "-" represents a compound in the form of a free base, whereas "HCl" represents a compound in the hydrochloride form.

TABLE

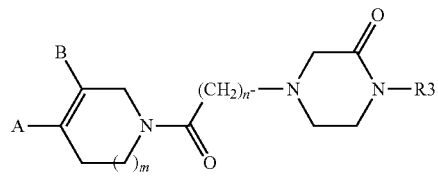

| No. | A | B | m | R3 | n | Salt | Mp | LCMS |
|---|---|---|---|---|---|---|---|---|
| 1 | Cl, CF₃ phenyl | H | 1 | pyridine-CF₃ | 1 | HCl | 210-211 | MH+ 547 r.t. 7.6 Method A |
| 2 | Cl, CF₃ phenyl | H | 1 | methylpyridine | 1 | HCl | 236-239 | MH+ 493 r.t. 6.5 Method A |

TABLE-continued
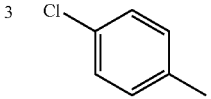
| No. | A | B | m | R3 | n | Salt | Mp | LCMS |
|---|---|---|---|---|---|---|---|---|
| 3 | 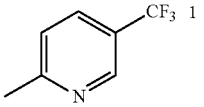 | H | 1 | 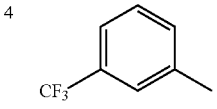 | 1 | — | 141-143 | MH+ 479 r.t. 7.9 Method C |
| 4 | 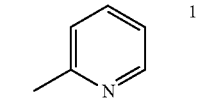 | H | 1 | 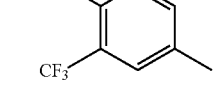 | 1 | — | 104-106 | MH+ 445 r.t. 5.4 Method A |
| 5 | 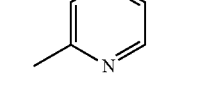 | H | 1 | 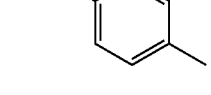 | 1 | HCl | 160-163 | — |
| 6 | 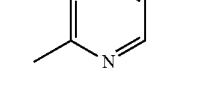 | H | 1 | 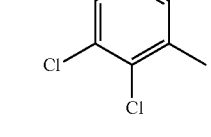 | 1 | — | 112-115 | MH+ 411 r.t. 5.4 Method A |
| 7 | 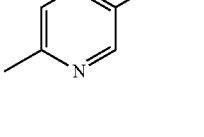 | H | 1 | 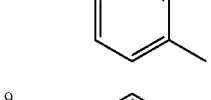 | 1 | — | 145-146 | MH+ 513 r.t. 6.9 Method A |
| 8 | 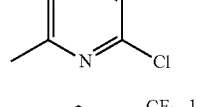 | H | 1 | 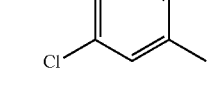 | 1 | HCl | 180-181 | MH+ 445 r.t. 7.2 Method A |
| 9 | 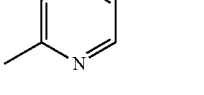 | H | 1 | 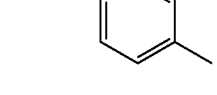 | 1 | HCl | 147-151 | MH+ 479 r.t. 7.3 Method A |
| 10 | 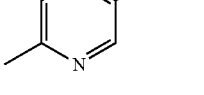 | H | 1 | 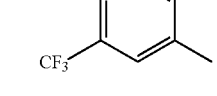 | 1 | — | 150-152 | MH+ 513 r.t. 7.9 Method C |
| 11 | 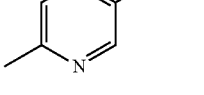 | H | 1 | 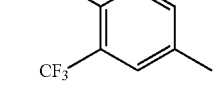 | 1 | Oxalate | 161-163 | MH+ 513 r.t. 6.8 Method A |
| 12 | 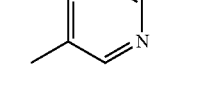 | H | 1 | 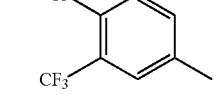 | 1 | — | — | M+ = 479 r.t. 5.7 Method A |
| 13 | 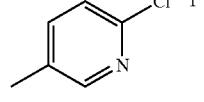 | H | 1 |  | 1 | fumarate | — | M+ = 513 r.t. 6.5 Method A |

TABLE-continued

| No. | A | B | m | R3 | n | Salt | Mp | LCMS |
|---|---|---|---|---|---|---|---|---|
| 14 | H | 3-CF₃-phenyl | 1 | 6-methyl-3-(5-CF₃)pyridyl | 1 | Oxalate | 172-173 | M+ = 513, r.t. 6.9, Method B |
| 15 | 3-OCF₃-phenyl | H | 1 | 6-methyl-3-(5-CF₃)pyridyl | 1 | Oxalate | 165-166 | M+ = 529, r.t. 7.1, Method A |
| 16 | 3-Cl,4-CF₃-phenyl | H | 0 | 6-methyl-3-(5-CF₃)pyridyl | 1 | — | 210-211 | M+ = 533, r.t. 7.0, Method A |
| 17 | 3,5-bis(CF₃)-phenyl | H | 1 | 6-methyl-3-(5-CF₃)pyridyl | 1 | Oxalate | 160-161 | M+ = 581, r.t. 8.1, Method C |
| 18 | 3,5-dimethyl-phenyl | H | 1 | 6-methyl-3-(5-CF₃)pyridyl | 1 | — | 130-131 | M+ = 459, r.t. 7.2, Method C |
| 19 | phenyl | H | 1 | 6-methyl-3-(5-CF₃)pyridyl | 1 | — | 140-142 | M+ = 445, r.t. 6.0, Method A |
| 20 | H | 2,3-dichloro-phenyl | 1 | 6-methyl-3-(5-CF₃)pyridyl | 1 | Oxalate | 177-178 | M+ = 513, r.t. 6.6, Method A |
| 21 | H | 3-MeO-phenyl | 1 | 6-methyl-3-(5-CF₃)pyridyl | 1 | Oxalate | 194-195 | M+ = 475, r.t. 5.9, Method A |

The compounds according to the invention were the subject of biochemical studies.

Cell Culture:

The SH-SY-5Y strain (human neuroblastoma) is cultured conventionally in a DMEM culture medium (Dulbecco's Modified Eagle's Medium) (Gibco BRL, France) containing FCS (5%) (foetal calf serum) (Boehringer Mannheim, Germany), sodium pyruvate (1 mM) and glutamine (4 mM) in culture flasks coated with collagen (Becton Dickinson, France).

The SK-N-BE parent strain (human neuroblastoma) and the Bep 75 clone, stably expressing the whole form of the human p75$^{NTR}$ receptor (SK-N-BE Bep 75) are cultured conventionally in a RPMI culture medium containing FCS (5%), sodium pyruvate (1 mM) and glutamine (4 mM). For the SK-N-BE Bep 75 cells, hygromycin (200 μl/20 ml of medium) is added as selection agent.

Study of the binding of the $^{125}$I NGF to the p75$^{NTR}$ receptor

The NGF binding study (nerve grown factor radiolabelled with iodine-125, Amersham—2000 Ci/mmol) is carried out on a cell suspension of the SK-N-BE Bep 75 strain in accordance with the method described by Weskamp (Neuron, 1991, 6, 649-663). The nonspecific binding is determined by measuring the total binding after one hour of pre-incubation with the cells at 37° C. in the presence of non-radiolabelled NGF (1 μM). The specific binding is calculated by the difference between the total binding measurement and the nonspecific binding measurement. The competition experiments are carried out using an iodinated NGF ($^{125}$I NGF) concentration of 0.3 nM. The concentrations inhibiting 50% ($IC_{50}$) of the binding of $^{125}$I NGF to the p75$^{NTR}$receptor, of the compounds according to the invention are low and vary from $10^{-6}$ to $10^{-11}$ M.

The compounds of formula (I) exhibit an activity in this test, with $IC_{50}$ values which range from $10^{-6}$ to $10^{-11}$ M.

For example, the compounds of examples Nos. 3 and 1 showed an $IC_{50}$ of 0.1 nM and 5.2 nM.

Study of the dimerization of the p75$^{NTR}$receptor independently of its ligand The p75$^{NTR}$receptor dimerization study is carried out on a cell suspension of the SK-N-BE Bep 75 strain. The cells (2.5 10$^4$cells/well) are placed in wells (96-well plate) for 24 h, and then preincubated for 1 h at 37° C. in the presence or absence of the compounds according to the invention. Supernatant is then added, this supernatant being derived from the culture of HEK293 human cells of renal origin expressing, after 48 h of transfection, and secreting a soluble form of the p75$^{NTR}$receptor (extracellular part of the receptor) coupled to an alkaline phosphatase, at the final concentration of 10 nM. The quantification of the specific binding of the soluble p75$^{NTR}$receptor to the receptor present on SK-N-BE Bep 75 cells is determined by measuring the alkaline phosphatase enzymatic activity after incubation of the cells for 1 hour at 37° C. in the presence of the supernatant. After filtration and transfer of the filters into 24-well plates, the alkaline phosphatase activity is determined by adding CDP-Star chemiluminescent substrate (ready-to-use, Roche). The concentrations inhibiting 50% ($IC_{50}$) of the dimerization of the p75$^{NTR}$receptor, of the compounds according to the invention, are low and vary from $10^{-6}$ to $10^{-11}$ M.

For example, the compounds of Examples No. 1, 2 and 3 showed respectively $IC_{50}$ values of 1.34 nM, 3.88 nM and 0.11 nM.

Measurement of Apoptosis

The cells (human neuroblastoma strains SH-SY-5Y and SK-N-BE Bep 75) are placed in 35 mm diameter Petri dishes (Biocoat collagen I), (10$^5$cells/well) in an appropriate culture medium containing 5% of FCS for 24 h. The culture medium is then removed, the cells are rinsed with PBS (Dulbecco's phosphate buffered saline), and then either fresh medium containing 5% FCS, or medium containing NGF (at the concentration of 10 ng/ml), or β-amyloid peptide (Aβ1-40) (at the concentration of 10 µM), is added, this being in the presence or absence of the compounds according to the invention. The degrees of apoptosis are measured 48 hours after the treatments in the case of the SH-SY-5Y strain, and 24 hours after the treatments in the case of the SK-N-BE Bep 75 strain, by quantification of the DNA fragment-associated cytoplasmic histones (cell death detection ELISA, Boehringer Mannheim, Germany). The degrees of apoptosis are expressed as amount of oligonucleosomes/10$^5$cells. Each value corresponds to the mean of 9 experimental points distributed over 3 independent experiments.

The compounds of formula (I) exhibit an inhibitory activity on NGF-induced apoptosis, with $IC_{50}$ values which range from $10^{-6}$ to $10^{-11}$ M. For example, the compound of Example No. 1 showed an $IC_{50}$ of 1.61 nM and the compound of Example No. 5 showed an $IC_{50}$ of 52 nM.

Thus, the binding of the compounds according to the invention to the p75$^{NTR}$receptor is reflected, on the one hand at the biochemical level, by inhibition of the dimerization of the receptor induced by neurotrophins, or independently of the ligand, and, on the other hand, at the cellular level, by inhibition of the proapoptotic effect mediated by the p75$^{NTR}$receptor.

Thus, according to one of the subjects of the present invention, the p75$^{NTR}$compounds of formula (I) exhibit a very advantageous inhibitory activity on receptor dimerization independently of its ligand.

The compounds according to the invention can therefore be used for the preparation of medicaments, in particular of medicaments for use in preventing or treating any pathological condition where the p75$^{NTR}$receptor is involved.

Thus, according to another of its aspects, a subject of the invention is medicaments which comprise a compound of formula (I), or an addition salt of the latter with a pharmaceutically acceptable acid.

According to another of its aspects, a subject of the invention is a compound of formula (I), or an addition salt of the latter with a pharmaceutically acceptable acid for the prevention or treatment of the pathological conditions indicated below.

Thus, the compounds according to the invention can be used, in humans or in animals, in the treatment or prevention of various p75$^{NTR}$-dependent conditions, such as central and peripheral neurodegenerative diseases, for instance senile dementia, epilepsy, Alzheimer's disease, Parkinson's disease, Huntington's chorea, Down's syndrome, prion diseases, amnesia, schizophrenia, depression, bipolar disorder; amyotrophic lateral sclerosis, multiple sclerosis; cardiovascular conditions, for instance post-ischaemic cardiac damage, cardiomyopathies, myocardial infarction, heart failure, cardiac ischaemia, cerebral infarction; peripheral neuropathies (of diabetic, traumatic or iatrogenic origin); damage to the optic nerve and to the retina (retinal pigment degeneration, glaucoma); retinal ischaemia; macular degeneration; spinal cord traumas and cranial traumas; atherosclerosis; stenoses; cicatrization disorders; alopecia.

The compounds according to the invention may also be used in the treatment of cancers, for instance lung cancer, thyroid cancer, pancreatic cancer, prostate cancer, cancer of the small intestine and of the colon, or breast cancer, or in the treatment of tumours, of metastases and of leukaemias.

The compounds according to the invention may also be used in the treatment of respiratory disorders, for instance pulmonary inflammation, allergy, asthma and chronic obstructive pulmonary disease.

The compounds according to the invention may also be used in the treatment of cutaneous pain (in the skin, the subcutaneous tissues and the associated organs), somatic pain, visceral pain (in the circulatory, respiratory, gastrointestinal, or urogenital system), and neurological pain.

The compounds according to the invention may be used in the treatment of chronic neuropathic and inflammatory pain and in the treatment of autoimmune diseases, such as rheumatoid arthritis.

The compounds according to the invention may also be used in the treatment of diseases such as ankylosing spondyl arthritis, psoriatic arthritis, or plaque psoriasis.

The compounds according to the invention may also be used in the treatment of bone fractures, or in the treatment or the prevention of bone diseases such as osteoporosis.

Thus, a subject of the present invention is a compound of formula (I) according to the invention for preventing or treating any pathological condition where the p75$^{NTR}$receptor is involved or more particularly the pathological conditions as indicated above.

According to another of its aspects, the present invention relates to pharmaceutical compositions comprising, as active ingredients, a compound according to the invention. These pharmaceutical compositions contain an effective dose of at least one compound according to the invention, or a pharmaceutically acceptable salt of said compound, and also at least one pharmaceutically acceptable excipient.

Said excipients are chosen, according to the pharmaceutical form and the method of administration desired, from among the customary excipients which are known to those skilled in the art.

In the pharmaceutical compositions of the present invention for oral, sublingual, subcutaneous, intramuscular, intravenous, topical, local, intratracheal, intranasal, transdermic or rectal administration, the active ingredient of formula (I) above, or salt thereof, may be administered in unit administration form, as a mixture with conventional pharmaceutical excipients, to animals and to human beings for the prevention or treatment of the disorders or diseases above.

The suitable unit administration forms comprise oral administration forms such as tablets, hard or soft gel capsules, powders, granules and oral solutions or suspensions, sublingual, buccal, intratracheal, intraocular and intranasal administration forms, forms for administration by inhalation, topical administration forms, parenteral, such as transdermal, administration forms, subcutaneous, intramuscular or intravenous administration forms, rectal administration forms and implants. For topical application, the compounds according to the invention may be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

The dose of active ingredient administered per day may reach 0.01 to 100 mg/kg, as one or more intakes, preferably 0.02 to 50 mg/kg. In general, the daily dose of the compound of the invention will be the lowest effective dose of the compound capable of producing a therapeutic effect.

There may be particular cases where higher or lower dosages are appropriate; such dosages do not depart from the context of the invention. According to the customary practice, the dosage suitable for each patient is determined by the physician according to the method of administration and the weight and response of said patient.

According to another of its aspects, the present invention also relates to a method of treating the pathological conditions indicated above, which comprises the administration, to a patient, of an effective dose of a compound according to the invention, or a pharmaceutically acceptable salt thereof.

What is claimed is:
1. A compound of formula (I):

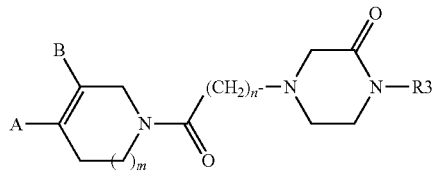

in which:
m is 0 or 1;
A is:

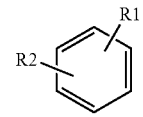

and B is a hydrogen atom
or
A is a hydrogen atom and B is:

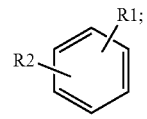

R1 and R2, which may be identical or different, are independently a hydrogen or halogen atom, a $C_1$-$C_4$ alkyl, $C_1$-$C_4$ fluoroalkyl, $C_1$-$C_2$ perfluoroalkyl or $C_1$-$C_4$ alkoxy group or a trifluoromethoxy group;
n is 1 or 2;
R3 is a group of formula:

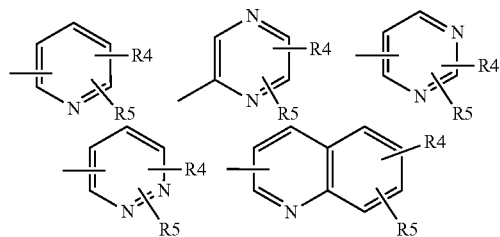

where R4 and R5, which may be identical or different, are located on any available positions, and are independently a hydrogen or halogen atom, a hydroxyl, a $C_1$-$C_4$ alkyl, $C_1$-$C_4$ fluoroalkyl, $C_1$-$C_2$ perfluoroalkyl, $C_1$-$C_4$ alkoxy group, a trifluoromethoxy group, a cyano group, a COOH, COOalkyl, $CONH_2$, CONR6R7 or NHCOR group,
R, R6 and R7 are a $C_1$-$C_6$ alkyl;
in the form of a base or of an acid addition salt.
2. A compound according to claim 1, wherein R4 and R5, which may be identical or different, are located on any available positions, and are independently $CONH_2$, CONR6R7 or NHCOR; in the form of a base or of an acid addition salt.

3. A compound according to claim 1, wherein:
m is 1;
A is:

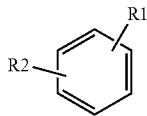

and B is a hydrogen atom;
R1 and R2, which may be identical or different, are independently a hydrogen or halogen atom, a $C_1$-$C_4$ alkyl, $C_1$-$C_4$ fluoroalkyl, $C_1$-$C_2$ perfluoroalkyl or $C_1$-$C_4$ alkoxy group or a trifluoromethoxy group;
n is 1 or 2;
R3 is a group of formula:

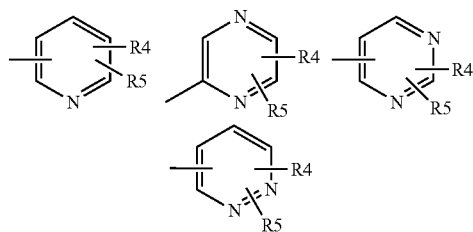

where R4 and R5, which may be identical or different, are located on any available positions and are independently a hydrogen or halogen atom, a hydroxyl, a $C_1$-$C_4$ alkyl, $C_1$-$C_4$ fluoroalkyl, $C_1$-$C_2$ perfluoroalkyl or $C_1$-$C_4$ alkoxy group, a trifluoromethoxy group, a cyano group, or a COOH or COOalkyl group;
in the form of a base or of an acid addition salt.

4. A compound according to claim 1, wherein R1 is other than H; in the form of a base or of an acid addition salt.

5. A compound according to claim 1, wherein R1 is in position -2-, -3- or -4- and is a chlorine atom, or a CF3 radical, and R2 is a hydrogen or a 3- or 4- Cl; in the form of a base or of an acid addition salt.

6. A compound according to claim 1, wherein R3 is a 2-pyridynyl or a 2-pyrimidinyl, each substituted with R4 and R5 as defined in claim 1; in the form of a base or of an acid addition salt.

7. A compound according to claim 1, wherein n=1; in the form of a base or of an acid addition salt.

8. A compound according to claim 1, wherein
R1 is 3-$CF_3$;
R2 is 4-chloro;
R3 is a 2-pyridyl residue 5-substituted with a $CF_3$; and
n =1;
in the form of a base or of an acid addition salt.

9. A compound according to claim 1 chosen from:
Compound No. 1: 4-{2-[4-(4-chloro-3-trifluoromethylphenyl)-3,6-dihydro-2H-pyridin-1-yl]-2-oxoethyl}-1-(5-trifluoromethylpyridin-2-yl)piperazin-2-one;
Compound No. 2: 4-{2-[4-(4-chloro-3-trifluoromethylphenyl)-3,6-dihydro-2H-pyridin-1-yl]-2-oxoethyl}-1-(5-methylpyridin-2-yl)piperazin-2-one;
Compound No. 3: 4-{2-[4-(4-chlorophenyl)-3,6-dihydro-2H-pyridin-1-yl]-2-oxoethyl}-1-(5-trifluoromethylpyridin-2-yl)piperazin-2-one;
Compound No. 4: 4-{2-oxo-2-[4-(3-trifluoromethylphenyl)-3,6-dihydro-2H-pyridin-1-yl]ethyl}-1-pyridin-2-ylpiperazin-2-one;
Compound No. 5: 4-{2-[4-(4-chloro-3-trifluoromethylphenyl)-3,6-dihydro-2H-pyridin-1-yl]-2-oxoethyl}-1-pyridin-2-ylpiperazin-2-one;
Compound No. 6: 4-{2-[4-(4-chlorophenyl)-3,6-dihydro-2H-pyridin-1-yl]-2-oxoethyl}-1-pyridin-2-yl-piperazin-2-one;
Compound No. 7: 4-{2-[4-(2,3-dichlorophenyl)-3,6-dihydro-2H-pyridin-1-yl]-2-oxoethyl}-1-(5-trifluoromethylpyridin-2-yl)piperazin-2-one;
Compound No. 8: 4-{2-[4-(4-chlorophenyl)-3,6-dihydro-2H-pyridin-1-yl]-2-oxoethyl}-1-(6-chloropyridin-2-yl)piperazin-2-one;
Compound No. 9: 4-{2-[4-(3-chlorophenyl)-3,6-dihydro-2H-pyridin-1-yl]-2-oxoethyl}-1-(5-trifluoromethylpyridin-2-yl)piperazin-2-one;
Compound No. 10: 4-{2-[4-(4-trifluoromethylphenyl)-3,6-dihydro-2H-pyridin-1-yl]-2-oxoethyl}-1-(5-trifluoromethylpyridin-2-yl)piperazin-2-one;
Compound No. 11: 4-{2-[4-(3-trifluoromethylphenyl)-3,6-dihydro-2H-pyridin-1-yl]-2-oxoethyl}-1-(5-trifluoromethylpyridin-2-yl)piperazin-2-one;
Compound No. 12: 4-{2-[4-(4-chloro-3-trifluoromethylphenyl)-3,6-dihydro-2H -pyridin-1-yl]-2-oxoethyl}-1-pyridin-3-yl-piperazin-2-one;
Compound No. 13: 1-(6-chloropyridin-3-yl)-4-{2-[4-(4-chloro-3-trifluoromethyl-phenyl)-3,6-dihydro-2H-pyridin-1-yl]-2-oxoethyl}piperazin-2-one;
Compound No. 14: 4-{2-oxo-2-[5-(3-trifluoromethylphenyl)-3,6-dihydro-2H-pyridin-1-yl]ethyl}-1-(5-trifluoromethylpyridin-2-yl)piperazin-2-one;
Compound No. 15: 4-{2-oxo-2-[4-(3-trifluoromethoxylphenyl)-3,6-dihydro-2H-pyridin-1-yl]ethyl}-1-pyridin-2-ylpiperazin-2-one;
Compound No. 16: 4-{2-[4-(4-chloro-3-trifluoromethylphenyl)-2,5-dihydropyrrol-1-yl]-2-oxoethyl}-1-(5-trifluoromethylpyridin-2-yl)piperazin-2-one;
Compound No. 17: 4-{2-[4-(3,5-bistrifluoromethylphenyl)-3,6-dihydro-2H-pyridin-1-yl]-2-oxoethyl}-1-(5-trifluoromethylpyridin-2-yl)piperazin-2-one;
Compound No. 18: 4-{2-[4-(3-methylphenyl)-3,6-dihydro-2H-pyridin-1-yl]-2-oxoethyl}-1-(5-trifluoromethylpyridin-2-yl)piperazin-2-one;
Compound No. 19: 4-{2-[4-phenyl-3,6-dihydro-2H-pyridin-1-yl]-2-oxoethyl}-1-(5-trifluoromethylpyridin-2-yl)piperazin-2-one;
Compound No. 20: 4-{2-oxo-2-[5-(2,3-dichlorophenyl)-3,6-dihydro-2H-pyridin-1-yl]ethyl}-1-(5-trifluoromethylpyridin-2-yl)piperazin-2-one; or Compound No. 21: 4-{2-oxo-2-[5-(3-methoxyphenyl)-3,6-dihydro-2H-pyridin-1-yl]ethyl}-1-(5-trifluoromethylpyridin-2-yl)piperazin-2-one;
in the form of a base or of an acid addition salt.

10. A process for preparing a compound of formula (I) according to claim 1, in which A, B, m, n, R3 are as defined in claim 1, comprising the step of reacting a compound of formula (IV)

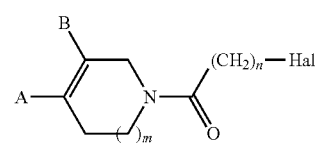

in which Hal is a halogen atom, and a compound of general formula (V):
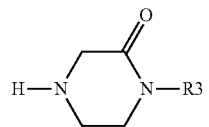
in which R3 is as defined in claim 1, in the presence of a base.
11. A pharmaceutical composition comprising a compound of formula (I) according to claim 1, or a pharmaceutically acceptable salt thereof, and at least one pharmaceutically acceptable excipient.
* * * * *

UNITED STATES PATENT AND TRADEMARK OFFICE
CERTIFICATE OF CORRECTION

PATENT NO. : 8,247,404 B2
APPLICATION NO. : 12/966408
DATED : August 21, 2012
INVENTOR(S) : Marco Baroni et al.

It is certified that error appears in the above-identified patent and that said Letters Patent is hereby corrected as shown below:

On the Title page, in field (56), in column 2, under "Other Publications", line 17, delete "Ennances" and insert -- Enhances --, therefor.

In column 4, line 44, delete "position-2-," and insert -- position -2-, --, therefor.

In column 4, line 45, delete "$CF_3$radical," and insert -- $CF_3$ radical, --, therefor.

In column 4, line 46, delete "4-halogen," and insert -- 4- halogen, --, therefor.

In column 4, line 48, delete "$CF_3$radical" and insert -- $CF_3$ radical --, therefor.

In column 4, line 49, delete "$CF_3$radical," and insert -- $CF_3$ radical, --, therefor.

In column 17, line 9, delete "$IC_{50}$values" and insert -- $IC_{50}$ values --, therefor.

In column 17, line 11, delete "$IC_{50}$of" and insert -- $IC_{50}$ of --, therefor.

In column 17, line 17, delete "$10^4$cells" and insert -- $10^4$ cells --, therefor.

In column 17, line 37, delete "$IC_{50}$values" and insert -- $IC_{50}$ values --, therefor.

In column 17, line 42, delete "($10^5$cells" and insert -- ($10^5$ cells --, therefor.

In column 17, line 56, delete "$10^5$cells." and insert -- $10^5$ cells. --, therefor.

In column 17, line 60, delete "$IC_{50}$values" and insert -- $IC_{50}$ values --, therefor.

In column 17, line 62, delete "$IC_{50}$of" and insert -- $IC_{50}$ of --, therefor.

Signed and Sealed this
Eighteenth Day of December, 2012

David J. Kappos
*Director of the United States Patent and Trademark Office*

CERTIFICATE OF CORRECTION (continued)
U.S. Pat. No. 8,247,404 B2

In column 17, line 63, delete "$IC_{50}$of" and insert -- $IC_{50}$ of --, therefor.

In column 18, line 5, delete "$p75^{NTR}$compounds" and insert -- compounds --, therefor.

In column 18, line 6, after "on" insert -- $p75^{NTR}$ --.

In column 21, line 15, in claim 3, delete "$_{C_1}$-$C_4$" and insert -- $C_1$-$C_4$ --, therefor.

In column 22, line 24, in claim 9, delete "2H -pyridin" and insert -- 2H-pyridin --, therefor.